United States Patent [19]
Grood et al.

[11] Patent Number: 5,018,514
[45] Date of Patent: May 28, 1991

[54] KNEE BRACE

[75] Inventors: Edward S. Grood, Cincinnati; David L. Butler, Fairfield, both of Ohio; D. Michael Ledyard, Grosse Pointe Park, Mich.; Steven D. Hoffman, Cold Springs, Ky.

[73] Assignee: Brace Technologies, Inc., Cincinnati, Ohio

[21] Appl. No.: 234,887

[22] Filed: Aug. 22, 1988

Related U.S. Application Data

[63] Continuation-in-part of Ser. No. 61,915, Jun. 11, 1987, abandoned.

[51] Int. Cl.$^5$ ............................................. A61F 5/00
[52] U.S. Cl. .............................. 128/80 C; 128/80 F; 128/88; 623/39
[58] Field of Search ............... 128/80 C, 80 F, 88; 623/39; 2/22, 24; 16/329

[56] References Cited

U.S. PATENT DOCUMENTS

| | | | |
|---|---|---|---|
| 3,187,347 | 6/1965 | Terron | 128/80 F |
| 3,581,741 | 6/1971 | Rosman et al. | 128/80 C |
| 3,799,158 | 3/1974 | Gardner | 128/80 C |
| 3,799,159 | 3/1974 | Scott | 128/80 C |
| 3,817,244 | 6/1974 | Taylor | 128/80 C |
| 3,898,709 | 8/1975 | Lewis et al. | 16/329 |
| 3,958,569 | 5/1976 | Vosburgh | 128/80 C |
| 4,088,130 | 5/1978 | Applegate | 128/80 F |
| 4,090,508 | 5/1978 | Gaylord | 128/80 C |
| 4,139,002 | 2/1979 | Almedia | 128/80 C |
| 4,271,831 | 6/1981 | Deibert | 128/80 C |
| 4,312,335 | 1/1982 | Daniell, Jr. | 128/80 C |
| 4,323,059 | 4/1982 | Rambert et al. | 128/80 C |
| 4,337,764 | 7/1982 | Lerman | 128/80 F |
| 4,340,041 | 7/1982 | Frank | 128/80 C |
| 4,370,977 | 2/1983 | Mauldin et al. | 128/80 F |
| 4,381,768 | 5/1983 | Erichsen et al. | 128/80 C |
| 4,433,679 | 2/1984 | Mauldin et al. | 128/80 F |
| 4,487,200 | 12/1984 | Feanny et al. | 128/80 C |
| 4,489,718 | 12/1984 | Martin | 128/80 C |
| 4,565,190 | 1/1986 | Pirmantgen et al. | 128/80 C |
| 4,617,920 | 10/1986 | Carsalade | 128/80 C |
| 4,632,097 | 12/1986 | Brooks | 128/80 C |
| 4,649,906 | 3/1987 | Spademan | 128/80 C |

FOREIGN PATENT DOCUMENTS 0478903  3/1954  Italy ..................................... 623/39

OTHER PUBLICATIONS

Townsend, M. A. et al., "Total Motion Knee Goniometry", J. Biomechanics, 1977, vol. 10, pp. 183-193.
Lew, W. D. et al., "A Comparison of Pistoning Forces in Orthotic Knee Joints", Orthotics and Prosthetics, vol. 36, No. 2, 1982, pp. 85-95.
Walker, P. S. et al., "External Knee Joint Design Based on Normal Motion", Jour. of Rehabil. Research and Development, vol. 22, No. 1, 1985, pp. 9-22.
"3D Dynamic Functional Knee Brace Fitter Instructions", 3D Orthopedic, Inc., Dallas, Tex. 75220. (Excerpts from brochures).
Lewis, J. L. et al., "A New Concept in Orthotics . . . Complete Orthosis", Orthotics and Prosthetics, vol. 38, No. 1, 1984, pp. 13-28.
Lewis, J. L. et al., "A New Concept in Orthotics Joint Design . . . Orthosis System", Orthotics and Prosthetics, vol. 37, No. 4, 1983, pp. 15-23.

Primary Examiner—Edgar S. Burr
Assistant Examiner—Moshe I. Cohen
Attorney, Agent, or Firm—Wood, Herron & Evans

[57] ABSTRACT

A knee brace for preventing abnormal anterior or posterior movement, and abnormal internal or external rotations, of the tibia relative to the femur includes a femoral cuff adapted for attachment to the thigh, a tibial cuff adapted for attachment to the calf and a pair of linkage assemblies interconnecting the cuffs. Each linkage assembly comprises a pair of link elements pivotally connected to one another, one of which is mounted to the femoral cuff and the other of which is slidable relative to the tibial cuff along an axis substantially parallel to the longitudinal axis of the tibia of the leg of a patient to prevent forces from being applied to the knee by the brace except in the anterior-posterior direction. The location of the hinge axis of the brace is adjustable relative to the flexion axis of the knee to impose an anterior or posterior force of variable magnitude on the tibia depending upon the ligament injury or deficiency.

23 Claims, 7 Drawing Sheets

KNEE BRACE

This application is a continuation-in-part of U.S. patent application Ser. No. 07/061,915, filed June 11, 1987 and entitled "Knee Brace", now abandoned.

FIELD OF THE INVENTION

This invention relates to knee braces, and, more particularly, to a knee brace for preventing abnormal anterior or posterior movements, and abnormal internal or external rotations, of the tibia relative to the femur in knees having ligament deficiencies.

BACKGROUND OF THE INVENTION

Ligaments compromise the fibrous connective tissues, which, in combination with joint geometry, are responsible for limiting the range of motion and for transmitting forces and moments across all skeletal joints of the body. One of the skeletal joints whose ligaments are susceptible to injury which often leads to chronic ligament deficiency is the knee joint. Knee orthoses or braces have been commercially available for some time to prevent abnormal motions and thus protect knee ligaments from being excessively stretched as they heal following injury or following surgical repair or reconstruction, to brace knees which are chronically unstable due to ligament deficiency and to prevent injury to the knee in the event of a fall or during athletic activities. Knee braces generally comprise a femoral cuff adapted for attachment to the thigh, a tibial cuff adapted for attachment to the calf and linkage which interconnects the femoral and tibial cuffs to permit pivotal movement therebetween.

Although often modeled as a hinge joint, the knee is in fact a polycentric joint whose motions are a combination of rolling and sliding movement between the contacting tibial and femoral condyle surfaces. In order to duplicate the complex anatomical motion of the knee, a knee brace must replicate the translational and rotational movements of the knee in three dimensions, i.e., the brace must replicate six component motions or "degrees of freedom". This task has proven to be virtually impossible to accomplish due to differences in the knee of one individual compared to another, and due to the difficulty in maintaining the knee brace at the proper position relative to the knee axis as that axis shifts position as the knee undergoes flexion-extension and internal-external rotation.

Prior art knee braces have been designed to locate the brace axis, i.e., the pivot axis of the linkage interconnecting the femoral and tibial cuffs, substantially coaxial with the flexion-extension axis of the knee with the lower leg in one position, or throughout partial movement of the leg. But the brace axis of such prior art knee braces is not maintained substantially coaxial with the knee axis throughout the complete range of normal translational and rotational movement of the knee. Nevertheless, the suspension system which mounts such prior art braces to the leg is designed to maintain the brace, and, in turn, the brace hinging axis, in an essentially fixed position on the leg. As a result, the brace fails to replicate normal movement of the knee joint and applies forces to the knee which are a combination of forces in the anterior-posterior direction and forces generally parallel to the longitudinal axis of the tibia. The resultant of these forces can interfere with the normal knee motion, create unnatural stresses on the knee, cause a loss of desired control of knee motion and induce a "pistoning" or shearing force between the cuffs of the brace and the skin. This pistoning or shearing force is believed to be a contributing factor to distal migration of the brace in which the brace tends to move toward the lower leg from its initial position. These problems contribute to wearer discomfort, skin irritation and possible damage to the knee joint.

Prior art braces are predominantly intended to control abnormal translation or rotation through the entire range of motion of the knee, but at least some braces have incorporated elements directed particularly to controlling selected knee motions for the protection of specific ligaments or ligament groups. For example, prior art knee braces are commercially available which incorporate a four-point suspension system for mounting the femoral cuff to the thigh and the tibial cuff to the calf. These braces are intended to control anterior or posterior translation of the tibia with respect to the femur for the protection of either the anterior or posterior cruciate ligaments.

Prior art four-point suspension systems for anterior cruciate ligament deficiencies, for example, employ four separate straps including a strap wrapped around the femoral cuff at the proximal-most part of the brace, a relatively inelastic strap wrapped posteriorly about the thigh immediately proximal to the patella, a strap wrapped anteriorly about the calf at the level of the proximal portion of the tibial cuff and a strap wrapped about the calf at the distal-most part of the tibial cuff of the brace. In response to an anterior force applied to the tibia by walking, climbing stairs or other movement, this arrangement of straps is intended to apply a restraining force to the tibia restricting its anterior translation relative to the femur. Knee braces for posterior cruciate ligament deficiencies have a similar construction except that the anterior and posterior straps are reversed.

One problem with the four-point suspension systems of prior art knee braces is that none account for the initial movement of the soft tissue when the brace is first loaded in response to an anterior or posterior force on the tibia. Restraining forces applied by the brace to the tibia must be transmitted through the soft tissue of the leg. Initially, the stiffness of the soft tissue is low and it compresses or deforms under load. Thus a relative motion occurs between the brace and the underlying bone whose motions are to be controlled. The restraining force provided by the brace depends upon amount of bone motion or soft tissue compression, the stiffness of the soft tissue and the brace design. As the tissue progressively deforms, its stiffness increases and so does the restraining force. Unfortunately, by the time soft tissue has been compressed sufficiently to effectively transmit forces from the brace to the tibia, unwanted translation of the tibia has occurred. As a result, prior art knee braces of this type are often ineffective in preventing abnormal anterior-posterior movement of the tibia and thus fail to protect the knee against such abnormal movement.

SUMMARY OF THE INVENTION

It is therefore among the objectives of this invention to provide a knee brace which limits abnormal anterior and posterior translation of the knee, which does not resist other normal knee motions or create unnatural stresses on the knee which result from resisting normal motions, which resists distal migration of the brace and which is adjustable to accommodate wearers having different amounts of anterior and posterior looseness and therefore different amounts of abnormal anterior-posterior knee motions to be controlled.

These objectives are accomplished in a knee brace of this invention which is predicated upon the concept of providing a restraining force to resist anterior or posterior translation of the tibia relative to the femur, and, in so doing, to also control the internal and external rotation of the tibia by limiting the anterior-posterior translation of the medial and lateral plateaus produced by the rotation, while otherwise permitting unrestricted movement of the knee. The knee brace comprises a femoral cuff adapted for attachment to the thigh of a patient, a tibial cuff adapted for attachment to the patient's calf and two linkages interconnecting the femoral and tibial cuffs which are located on opposite sides of the cuffs. Each of the linkages comprises a femoral link element and a tibial link element which are connected together at one of their ends by a hinging mechanism for pivotal motion therebetween. The opposite end of the femoral hinge element is pivotally mounted to the femoral cuff, and the opposite end of the tibial link element is carried by the tibial cuff. The tibial link element includes structure for permitting axial, sliding motion thereof relative to the tibia of the patient along an axis substantially parallel to the longitudinal axis of the tibia.

The structure of the linkages interconnecting the femoral cuff and tibial cuff provide for two distinct motions in the knee brace of this invention. The hinging mechanism interconnecting the femoral link element and tibial link element allows for rotation about a hinge axis primarily oriented in a side-to-side or lateral-medial direction, this rotation permitting flexion and extension of the knee. The sliding, axial motion of the tibial link element permits translation of the hinge relative to the tibial cuff in a direction generally parallel to the longitudinal axis of the tibia. In addition, in one presently preferred embodiment, the connection between the tibial link element and tibial cuff also permits rotation of the hinge about the longitudinal axis of the tibia.

In one broad aspect of this invention, the construction of the knee brace herein avoids the imposition of undesirable constraining forces on the knee which could create unnatural movement or unnatural forces on the knee. Depending upon the ligament of ligament group injured, e.g., posterior cruciate ligament or anterior cruciate ligament, the knee brace of this invention applies a force to the tibia which replaces that of the injured ligament without interfering with the other component motions of the knee. This is achieved by "decoupling" the anterior-posterior forces applied to the knee by the knee brace from the forces applied by the brace along an axis substantially parallel to the axis of the tibia.

The feature of this invention which permits a decoupling of the forces applied to the knee is the sliding movement of the tibial link element of each linkage assembly relative to the tibia along an axis substantially parallel to the longitudinal axis of the tibia. This feature is an important distinction and improvement over prior art knee braces. Prior art knee braces generally include femoral and tibial cuffs which are mounted in a fixed position to the leg, and employ a linkage structure interconnecting the femoral and tibial cuffs having a hinge which is mounted in a fixed position relative to the flexion-extension axis of the knee once the brace is secured on the leg. Because of the polycentric nature of the knee joint, it is exceedingly difficult to position the brace axis or hinge of the linkage structure colinear with the flexion axis of the knee throughout the entire range of motion of the knee. When the brace and knee axes are not aligned, the brace is not able to reproduce or follow the normal motion of the knee as the knee is flexed and extended. The different motions of the brace and the knee result in the brace applying a force to the calf. This force has a component acting in the anterior-posterior direction of the tibia and a component acting substantially parallel to the longitudinal direction of the tibia. The resultant of these forces applied by prior art knee brace to the knee creates unnatural movements of the knee which can contribute to discomfort, further damage to the knee, and brace migration.

This invention eliminates such a deficiency in prior art knee braces by permitting sliding motion or translation of the tibial linkage element of the linkage interconnecting the cuffs with respect to the tibial cuff and the tibia. This sliding motion "decouples", or eliminates as a component force, the force applied by the brace along an axis substantially parallel to the longitudinal axis of the tibia. As a result, the primary forces applied to the knee by the brace of this invention are in an anterior or posterior direction. The knee joint is otherwise free to move without restriction from the brace so as to avoid the imposition of unnatural forces to the knee.

Sliding motion of the tibial linkage elements relative to the tibia along an axis parallel to the longitudinal axis of the tibia can be accomplished in a number of different ways. In one presently preferred embodiment, each of the tibial link elements comprises a rod mounted at one end to the hinge of the brace, and a sleeve carried on one side of the tibial cuff which is formed with a stepped throughbore adapted to receive the rod. The sleeve of each tibial link element carried on the tibial cuff is axially movable relative to the rod mounted to the hinge as the knee moves in flexion and extension to eliminate any force on the knee applied along the longitudinal axis of the tibia.

In an alternative embodiment, the position of the rod and sleeve of each tibial link element can be reversed. That is, a rod is fixedly mounted on either side of the tibial cuff and a hollow sleeve is connected at one end to the brace hinge and receives the rod within its opposite end. The rod is axially movable relative to the sleeve when the knee moves in flexion or extension to obtain the sliding motion of the tibial link element as in the previous embodiment.

In either of the above-described embodiments, the rod of each tibial link element is preferably cylindrical in shape and rotatable within a sleeve to permit rotation of the hinge about the longitudinal axis of the tibia. Alternatively, a key-keyway connection is provided between the sleeve and rods of the tibial link elements, or the sleeve and rods are non-cylindrical, so that rotation of the hinge relative to the tibia is prevented. Additionally, the rods of the tibial link elements in each of the aforementioned embodiments are formed with stops which engage the sleeve to limit the extent of axial movement of the rods therewithin and to prevent disengagement of the rod from the sleeve.

The sliding motion of the tibial link elements relative to the tibia can also be achieved by further alternative embodiments. In another embodiment, the tibial link elements each comprise upper and lower flat bars. The lower bar has a distal end fixed to the tibial cuff and a proximal end formed with an elongated slot. The upper bar has a distal end located adjacent the proximal end of the lower bar and a proximal end connected to the hinge of the brace. A plate interconnects the proximal end of the lower bar and the distal end of the upper bar to permit axial movement therebetween. The plate is formed with spaced bores which receive screws extending through the slot in the lower bar and into the distal end of the upper bar. Sliding motion of the lower bar relative to the upper bar is obtained in response to movement of the knee in flexion or extension as the slotted portion of the lower bar slides along the screws holding the plate to the upper bar.

A still further embodiment which permits sliding motion of the tibial link elements comprises a cam which replaces the brace hinge of the previously described embodiments. The cam is a circular plate eccentrically mounted to the distal end of the femoral link element on either side of the brace. The cam is formed with an arcuate groove, radially spaced from the center of the cam, within which the proximal end of the tibial link element is slidably mounted by a pivot arm. The opposite, distal end of the tibial link element is fixed to the tibial cuff. The pivot arm is rotatably pinned to the proximal end of the tibial link element at one end, and its opposite end is pivotally mounted to the center of the cam. In response to flexion or extension of the knee, the proximal end of the tibial link element moves along the slot in the cam which produces a substantially axial movement of the tibial link element relative to the longitudinal axis of the tibia.

In another broad aspect of this invention, a restraining force is applied by the brace which compresses the soft tissue of the leg relative to the underlying bones when the brace is loaded in response to an anterior or posterior force on the tibia. Adjustment of the restraining force provided by the brace is accomplished by adjusting the location of the hinge axis of the brace relative to the flexion axis of the knee. An intentional misalignment of the brace axis and flexion-extension axis produces a pre-load or initial force to compress the soft tissue of the leg as the knee is flexed or extended. Adjustment structure associated with the brace is operable to vary the location of the brace axis relative to the flexion-extension axis and thus vary the magnitude of the restraining force applied to the knee depending upon the amount of abnormal joint looseness and the compliance of the soft tissues.

For example, for patients having an anterior cruciate ligament deficiency, the location of the hinge axis on the femur is adjusted so that it is located proximal and distal with respect to the normal flexion-extension axis of the knee. This intentional misalignment of the brace axis and flexion axis of the knee results in the imposition of a restraining force on the tibia by the brace in the posterior direction to compress the soft tissue to avoid relative motion between the brace and the underlying bone when the brace is first loaded, i.e., during initial movement of the knee, and to thereafter prevent the knee from giving way or undergoing abnormal anterior movement. This posterior restraining force increases as the knee is extended and is greatest at full extension where an intact anterior cruciate ligament normally provides the greatest resistant to anteriortibial translation. Although the hinge axis of the brace is misaligned from the knee axis in this embodiment, the sliding connection between the tibial link elements and tibial cuff prevents the application of forces by the brace to the knee in a direction substantially parallel to the longitudinal axis of the tibia, as described above.

One embodiment of the adjustment structure herein for varying the anterior-posterior position on the femur of the brace pivot axis consists of the femoral link elements which are pivotally mounted at one end on either side of the femoral cuff by a pin, rivet or similar fastener. The opposite end of each femoral link element is hinged to a tibial link element and swings or pivots about the pin connection to the femoral cuff thereby varying the anterior-posterior position of the hinge relative to the femur. Straps connected between the femoral link elements, and placed around the anterior and posterior aspects of the thigh, maintain the femoral link elements in the adjusted angular position with respect to the femoral cuff so that the hinge axis of the brace is located in the desired anterior or posterior position relative to the flexion axis of the knee.

Alternatively, the anterior-posterior position of the brace pivot axis is adjustable by rotating the cam about its eccentric connection to the femoral link elements in the embodiment wherein the cam replaces the hinge. Such rotation of the cam varies the anterior-posterior position of its center about which the tibial link elements are pivotal.

Adjustment structure is also provided for varying the proximal-distal location on the femur of the brace pivot axis relative to the flexion-extension axis of the knee. In one embodiment, the proximal end of each femoral link element is formed with an axial slot which receives a screw or similar fastener mounted to the femoral cuff. This connection permits both angular and axial adjustment of the femoral link element relative to the femoral cuff to vary both the anterior-posterior and proximal-distal position of the hinge. Alternatively, the location of the axial slot in each femoral link element can be moved intermediate its proximal and distal ends to permit proximal-distal adjustment thereat. In this embodiment, each femoral link element includes an upper bar and a lower bar, with the upper bar being angularly adjustable at its proximal end to the femoral cuff and the lower bar being connected to the hinge or cam at its distal end. The opposite, free ends of the upper and lower bars of the femoral link elements are attached together by a screw or similar fastener which extends through an axial slot formed in one of the bars. This slotted connection between the upper and lower bars of the femoral link elements permits axial adjustment of the hinge, and thus the brace pivot axis, in the anterior-posterior direction.

Normally, the brace is applied with the patient in the sitting position and the knee flexed approximately 90°. With the knee in this position, proximal-distal adjustment of the position of the brace axis obtained by either proximal-distal movement of the femoral link element as described above, or repositioning of the femoral cuff on the thigh, produces an anterior-posterior adjustment of the location on the tibia of the brace pivot axis relative to the flexion-extension axis of the knee. Any change in the anterior-posterior position on the tibia of the brace pivot axis imposes a similar change in position of the proximal end of the tibial link elements which are connected to the hinge mechanism. This change in anterior or posterior position on the tibia of the proximal end of the tibial link elements can cause the tibial cuff to cock or pull away from the calf instead of lying flat.

As a result, structure is provided to permit adjustment of the position of the proximal end of the tibial link elements so that the tibial cuff will lie flat on the calf. In one presently preferred embodiment, the distal end of the tibial link element is pivotally mounted to the tibial cuff and an extension is mounted to the tibial link element which is formed with an arcuate slot having a screw extending therethrough. Movement of the tibial link element relative to the tibial cuff along the slot in its extension permits angular adjustment of the proximal end of the tibial link element to accommodate a change in the anterior-posterior location on the tibia of the brace pivot axis. Such adjustment ensures that the tibial cuff will remain comfortably fitted to the calf.

Alternatively, each tibial link element is formed with a fixed position pivot between their proximal end connected at the brace hinging mechanism, and their distal end connected to the tibial cuff. This fixed position pivot permits angular adjustment of the proximal end of the tibial link elements in the event of an anterior-posterior adjustment of the location of the brace hinge axis to ensure the tibial cuff properly fits on the calf.

DESCRIPTION OF THE DRAWINGS

The structure, operation and advantages of a presently preferred embodiment of this invention will become further apparent upon consideration of the following description, taken in conjunction with the accompanying drawings, wherein.

DETAILED DESCRIPTION OF THE INVENTION

Figures 1, 1A:
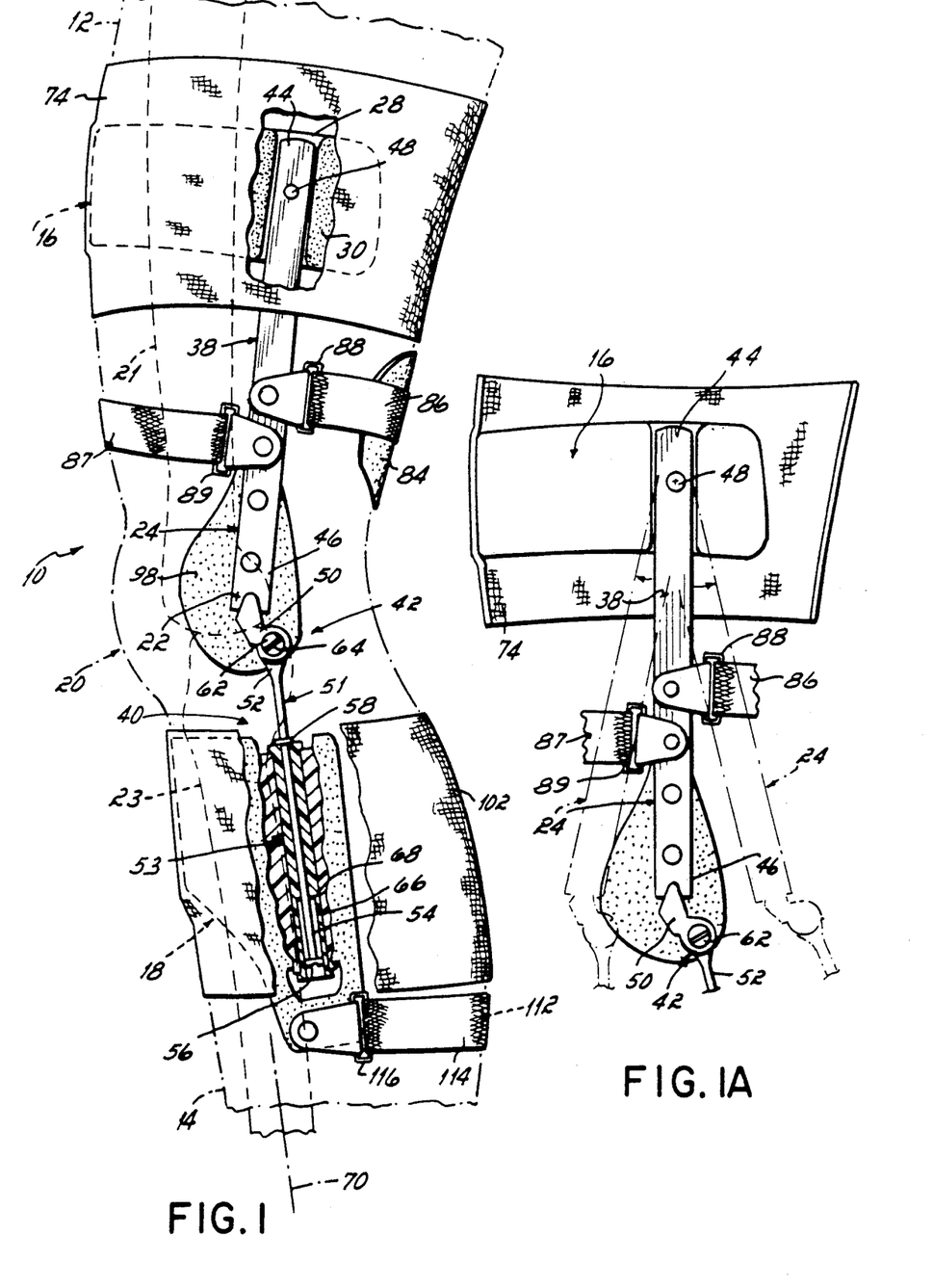
FIG. 1 is a diagrammatic view of the side of a leg having the knee brace of this invention mounted thereto.
FIG. 1A is a view of a portion of FIG. 1 showing the variable position of the femoral link element of the knee brace of this invention.
Figure 3:
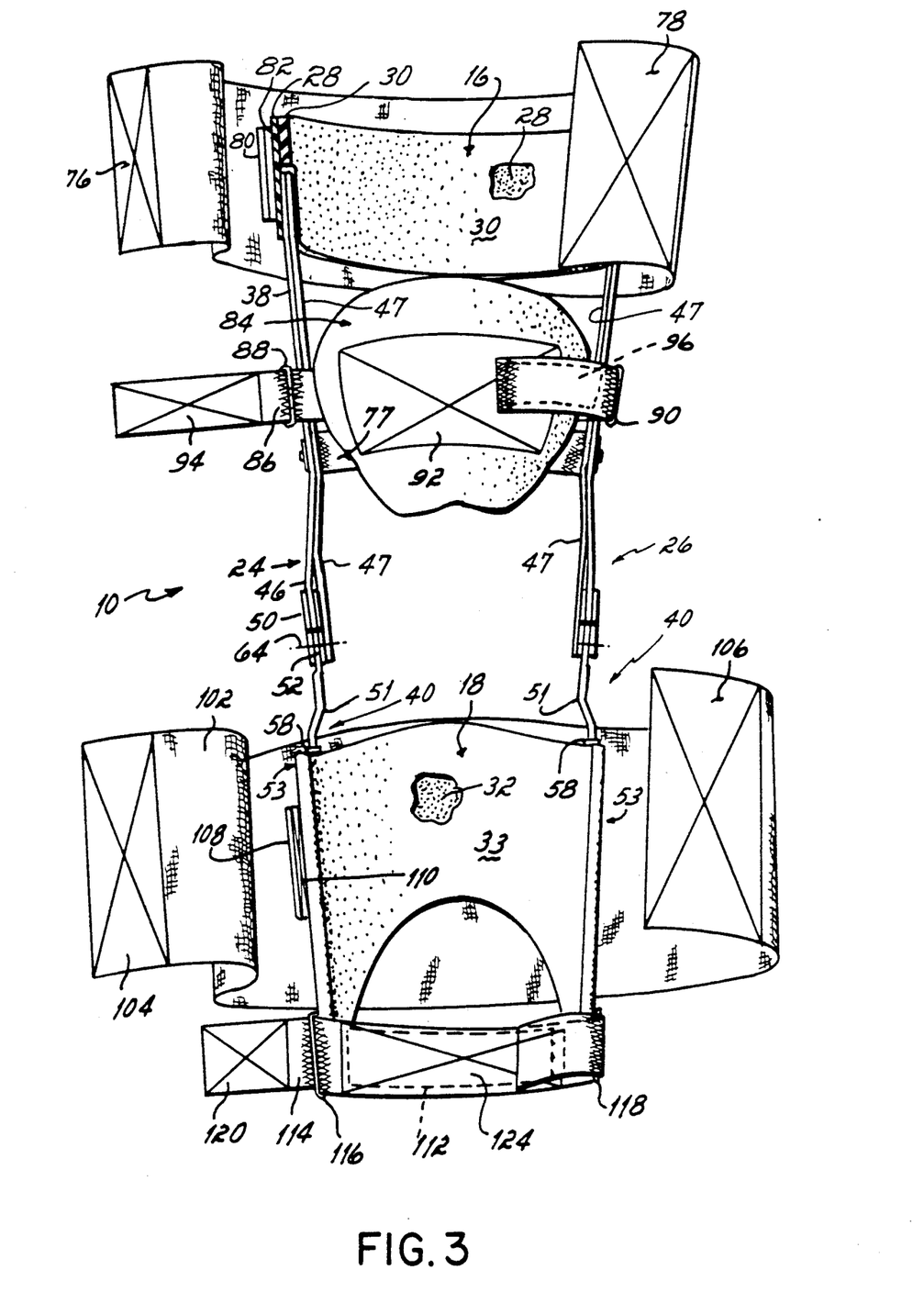
FIG. 3 is a rear view of the knee brace herein showing the straps in an unsecured position and each of the linkages which connect the femoral and tibial cuffs.

Referring now to FIGS. 1 and 3, the knee brace 10 of this invention is illustrated in position on the thigh 12 and calf 14 of a patient. The knee brace 10 comprises a femoral cuff 16 located on the anterior aspect of the thigh 12 and a tibial cuff 18 located on the anterior aspect of the calf 14. The femoral and tibial cuffs 16, 18 are spaced proximally and distally, respectively, of the knee joint 20 connecting the femur 21 and tibia 23. The flexion-extension axis of the knee joint 20 is indicated at 22. The femoral and tibial cuffs 16, 18 are interconnected by a pair of linkage assemblies 24, 26 as described in detail below.

In a presently preferred embodiment, the femoral cuff 16 extends approximately 180° about the anterior aspect of the thigh 12 and comprises a substantially semicircular-shaped plate 28, preferably formed of a lightweight material such as aluminum, plastic or composite, covered by a resilient pad 30 of a cushioning material. The tibial cuff 18 extends approximately 180° about the anterior aspect of the calf 14 and comprises a generally semicircular-shaped section 32 covered by a cushioning material 33.

Figure 2:
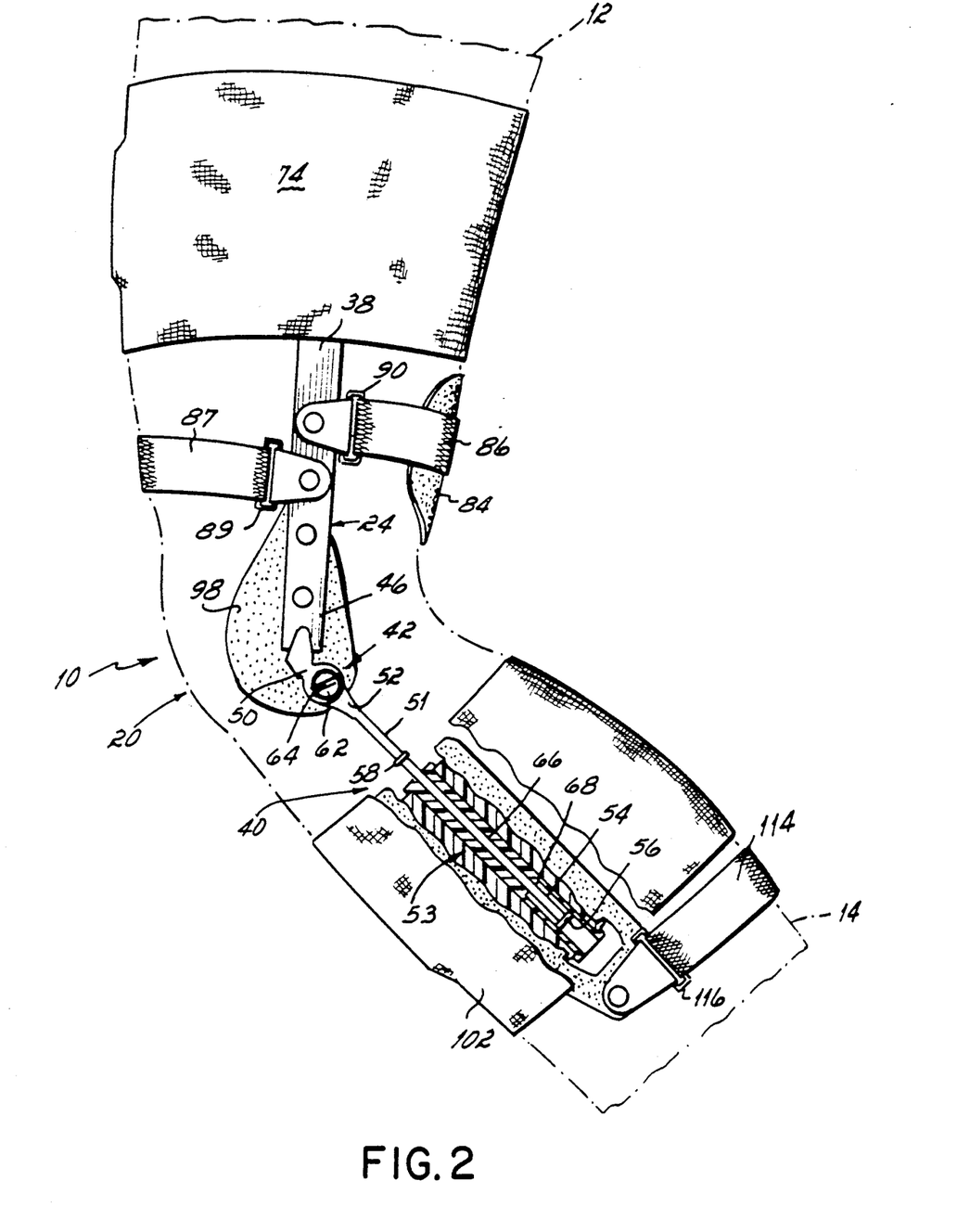
FIG. 2 is a view similar to FIG. 1 with the knee partially flexed.

Referring now to FIGS. 1, 2 and 3, the linkage assemblies 24, 26 are shown mounted to opposite sides of the femoral cuff 16 and tibial cuff 18. Linkage assembly 26 is identical to linkage assembly 24 as shown in FIG. 3 except for contours which adapt assemblies 24, 26 to fit against opposite sides of the knee, and thus only linkage assembly 24 will be described in detail herein it being understood that the same description and reference numbers apply to linkage assembly 26.

Linkage assembly 24 comprises a femoral link element 38 and a tibial link element 40 which are interconnected by a hinge 42 for pivotal motion therebetween. The femoral link element 38 is preferably a bar formed of a lightweight material such as aluminum, plastic or composite having a proximal end 44 and a distal end 46. The proximal end 44 is pivotally connected by a rivet or pin 48 to one side of the femoral cuff 16. The distal end 46 of the femoral link element 38 is fixedly mounted within an upper yoke 50 which forms a part of the hinge 42.

The tibial link element 40 comprises a cylindrical rod 51 and a sleeve 53 mounted to one side of the tibial cuff 18. The rod 51 has an upper end 52 formed with a bore (not shown) and a lower end 54 to which a screw 56 is mounted. A ring 58 extends radially outwardly from the exterior surface of the rod 51 approximately a third of the way down from its upper end 52, for purposes to become apparent below. As illustrated in FIGS. 1 and 3, the upper end 52 of rod 51 is inserted within the yoke 50 of the hinge 42 and is secured thereto by a screw 62 to pivotally interconnect the femoral and tibial link elements 38, 40. The axis of screw 62 forms the hinge axis 64 of the brace 10, as shown in FIG. 3, which permits flexion-extension of the knee joint 20.

The portion of rod 51 from the ring 58 downwardly, as viewed in FIGS. 1 and 2, is received within the sleeve 53 of the tibial link element 40 carried on the tibial cuff 18. The sleeve 53 is formed with a stepped throughbore 66 which defines a shoulder 68 in its interior. In a presently preferred embodiment, the sleeve 53 is formed of a rigid plastic material having a low coefficient of friction which is riveted or similarly affixed to the tibial cuff 18.

The rod 51 is axially slidable within the throughbore 66 of the sleeve 53 substantially parallel to the longitudinal axis 70 of the tibia 23. As illustrated in FIG. 2, as the knee 20 is flexed, the rod 51 of tibial link element 40 slides upwardly within the sleeve 53 with the screw 56 at its lower end 54 moving toward the shoulder 68. The shoulder 68 provides a stop which engages the screw 56 to limit the extent of axial movement of the rod 51 within the sleeve 53, and to prevent disengagement of the rod 51 from the sleeve 53. Additionally, the ring 58 engages the top of sleeve 53 as shown in FIG. 1 to limit the downward axial movement of the rod 51 therewithin.

For the reasons discussed above, it is desirable to "decouple" the forces applied by the brace 10 to the knee joint 20 in a direction parallel to the longitudinal axis 70 of the tibia 23 from those forces applied to the knee joint 20 in a direction perpendicular to the longitudinal axis 70, i.e., a direction oriented primarily in the anterior-posterior direction with respect to the tibia 23. The sliding motion between the rod 51 and sleeve 53 of the tibial link element 40 provides this decoupling of the forces applied by the brace 10 to the knee joint 20. Additionally, in order to ensure smooth sliding motion of the rod 51 within the sleeve 53, the cylindrical-shaped rod 51 is also rotatable within the throughbore 66 formed in the sleeve 53. This resists binding between the rod 51 and sleeve 53 in the event of misalignment of the brace 10 on the leg or any other problem which would tend to cock the rod 51 within the sleeve 53 and create an unwanted force in a direction parallel to the axis of the tibia 23.

Figure 4:
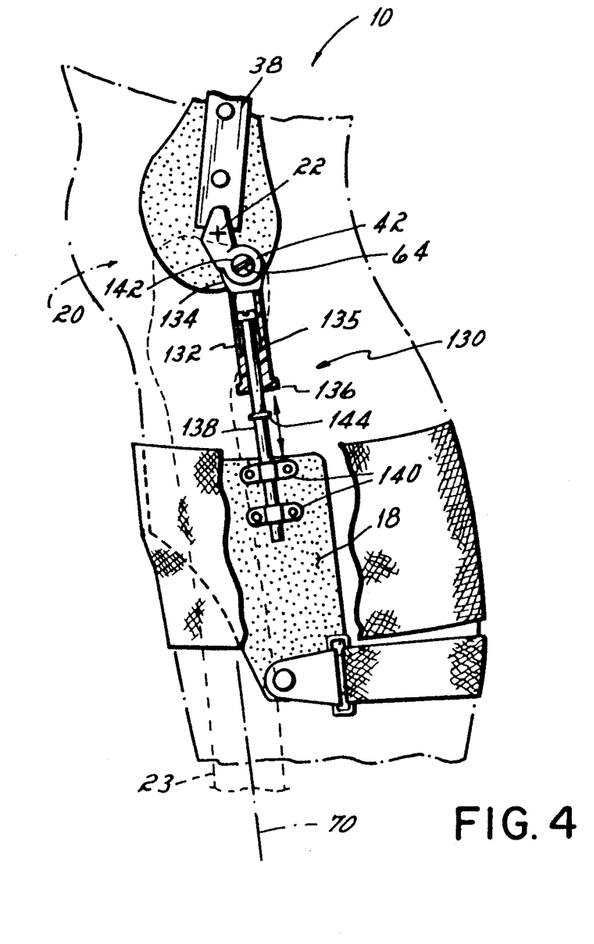
FIG. 4 is a partial view of the knee brace herein with an alternative embodiment of structure for permitting sliding motion of the tibial link elements relative to the tibia.

Referring now to FIGS. 4-6C, alternative embodiments are shown in which the forces applied by the brace 10 to the knee joint 20 in a direction parallel to the longitudinal axis 70 of the tibia 23 are decoupled from those forces applied to the knee joint in an anterior-posterior direction. In FIG. 4, a tibial link element 130 is provided which is essentially the reverse construction of tibial link element 40. Tibial link element 130 comprises a hollow sleeve 132 having a proximal end 134 connected to the hinge 42 of the brace 10, and a stepped throughbore forming a shoulder 135 in the interior of sleeve 132. The distal end 136 of the hollow sleeve 132 slidably receives a rod 138 which is fixed by brackets 140 to the tibial cuff 18. In response to flexion or extension of the knee, the hollow sleeve 132 is axially movable with respect to the rod 138 along an axis substantially parallel to the longitudinal axis 70 of the tibia 23. Preferably, the proximal end of rod 138 includes a screw 142 or similar stop which contacts the internal shoulder 135 of sleeve 132 to prevent disengagement of the sleeve 132 and rod 138. Additionally, the rod 138 includes a ring 144 on its outer surface which contacts the distal edge 136 of the sleeve 132 to limit the extent of movement of the rod 138 therein.

Figures 5, 5A:
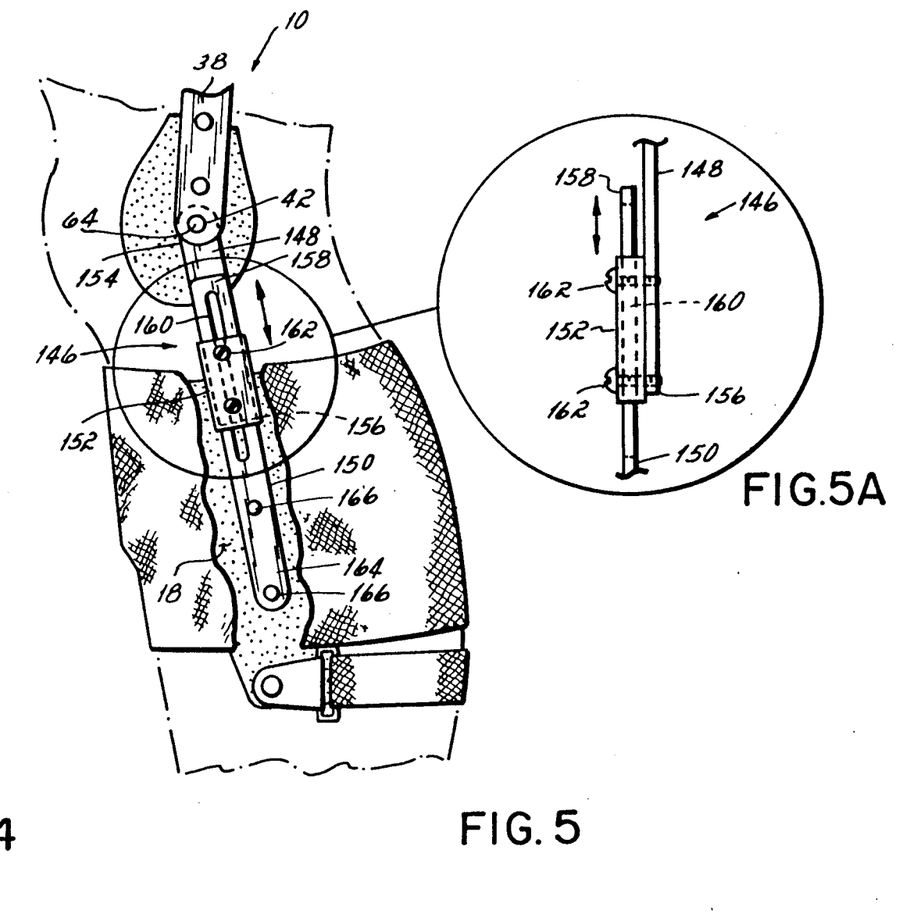
FIG. 5 is a partial view of the knee brace herein with a second alternative embodiment of structure for permitting sliding motion of the tibial link elements relative to the tibia.
FIG. 5A is an enlarged, side elevational view of the circled portion of FIG. 5.

Another alternative embodiment of structure for providing sliding motion of the brace 10 relative to the tibia 23 is illustrated in FIGS. 5 and 5A. In this embodiment, a tibial link element 146 comprises an upper bar 148, a lower bar 150 and a connector plate 152. The upper bar 148 has a proximal end 154 mounted to the hinge 42 of the brace 10. The opposite, distal end 156 of the upper bar 148 is mounted to the proximal end 158 of the lower bar 150 by the connector plate 152. The proximal end 158 of the lower bar 150 is formed with an elongated slot 160 and a pair of fasteners 162 extend from the connector plate 152, through the elongated slot 160 and into the distal end 156 of upper bar 148. The opposite, distal end 164 of the lower bar 150 is mounted by pins or rivets 166 to the tibial cuff 18.

In response to the movement of the knee in flexion or extension, the lower bar 150 of tibial link element 146 is axially movable with respect of the upper bar 148. The lower bar 150 slides along the fasteners 162 as it moves in the proximal or distal direction. The edges of the elongated slot 160 provide stops to limit the sliding or axial movement of the lower bar 150 with respect of the upper bar 148.

Referring now to FIGS. 6A-6D, a still further embodiment is illustrated of structure for permitting sliding motion of the tibial link element with respect of the longitudinal axis 70 of the tibia 23. The embodiment of FIGS. 6A-6D differs from those described above in that the hinge 42 is eliminated and replaced by a camming arrangement as described below.

Figures 6A, 6B, 6C, 6D:
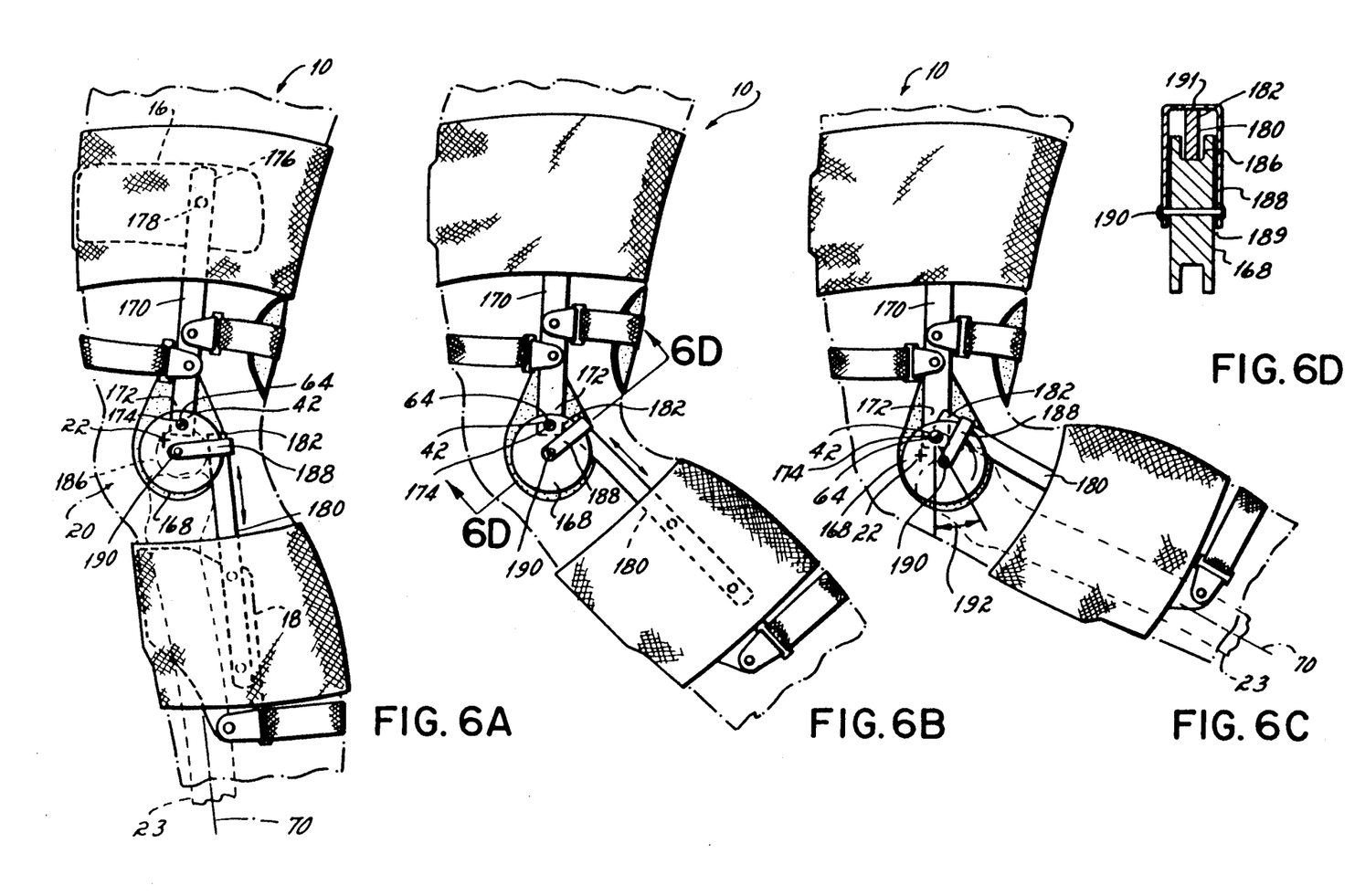
FIG. 6A is a partial view of the knee brace herein with still another alternative embodiment of structure for permitting sliding motion of the tibial link elements relative to the tibia.
FIG. 6B is a view similar to FIG. 6A except with the knee having moved from the fully extended position in FIG. 6A to a partially flexed position in FIG. 6B.
FIG. 6C is a view similar to FIG. 6B, with the leg in a partially flexed position, except the cam has been rotated about its eccentric connection to the femoral link element to vary the anterior-posterior position of the proximal end of the tibial link element.
FIG. 6D is an enlarged cross sectional view taken along line 6D—6D of FIG. 6B.

Referring initially to FIGS. 6A and 6B, a cam 168 in the form of a circular plate is mounted on either side of the knee, only one of which is shown in the Figs. for ease of illustration. A femoral link element 170 is mounted at its distal end 172 to the cam 168 by a screw 174. The opposite, proximal end 176 of the femoral link element 170 is pivotally mounted by a pin 178 to the femoral cuff 16. The straps associated with the femoral cuff 16 and femoral link element 170 are identical to those described in more detail below in connection with the embodiments of FIGS. 1-3. As shown in FIGS. 6A and 6B, the connection of the femoral link element 170 to cam 168 is offset or eccentric relative to the center of the cam 168 for purposes to become apparent below.

A tibial link element 180 is provided in this embodiment having a proximal end 182 carried within a circumferential groove 186 formed in the outer edge of cam 168. The tibial link element 180 is held within the groove 186 by a U-shaped pivot arm 188 having an open end 189 connected at the center of the cam 168 by a pin 190 and a closed end 191 extending around the proximal end 182 of tibial link element 180. See FIG. 6D.

As shown in FIGS. 6A and 6B, in response to movement of the knee 20 in flexion, the tibial link element 180 moves in a proximal direction along an axis substantially parallel to the longitudinal axis 70 of the tibia 23. Such motion is permitted by the sliding movement of the tibial link element 180 in the groove 186 formed in the cam 168. The pivot arm 188, which is rotatable about the pin 190 connected to cam 168, prevents the tibial link element 180 from disengaging the circumferential groove 186.

Referring again to FIGS. 1-3, the femoral and tibial cuffs 16, 18, and their linkage assemblies 24, 26, are mounted to the leg by a series of straps. Although not shown in detail, the same strap arrangement described below with reference to FIGS. 1-3 is identical to that employed in the embodiment of FIGS. 4-7B. The straps, in combination with cuffs 16, 18, form a four-point suspension system of the type generally known in the prior art which forms no part of this invention per se and is thus described briefly herein.

A femoral cuff strap 74 is provided having strips 76, 78 of VELCRO fabric fastening material connected at each end to its inner and outer surfaces, respectively. The trademark VELCRO is meant to refer to a fastening material consisting of interlocking plastic hoops and hooks. A VELCRO strip 80 is connected to the inner surface of femoral cuff strap 74 at one end. The femoral cuff strap 74 is mounted to one side of femoral cuff 16 by first connecting VELCRO strip 80 to a cooperating VELCRO strip 82 mounted on the femoral cuff 16, and then wrapping the strap 74 around the posterior aspect of the thigh 12. The opposite end of femoral cuff strap 74 is secured by connecting the VELCRO strip 76 mounted on the inner surface of strap 74 at such opposite end to the VELCRO strip 78 on the outer surface of strap 74. Preferably, the femoral cuff strap 74 is formed of an elastic material having a relatively high coefficient of friction to aid in maintaining the femoral cuff 16 in a substantially fixed position on the thigh 12.

Located distally of the femoral cuff 16 is a femoral pad 84, preferably made of a cushioning material, which is formed to rest against a portion of the posterior aspect of the thigh 12. The femoral pad 84 is mounted to the thigh 12 beneath a substantially inelastic strap 86. One end of strap 86 extends through a ring 88 riveted to the femoral link element 38 of linkage assembly 24, and the opposite end of strap 86 extends through a ring 90 riveted to the femoral link element 38 of linkage assembly 26. See FIG. 3. The outer surface of the femoral pad 84 is provided with a VELCRO strip 92 which connects to cooperating VELCRO strips 94 mounted on strap 86 to secure the femoral pad 84 to the leg.

The femoral link elements 38 are also held in place by a strap 87 connected between femoral links 38 by rings 89. This strap is to be wrapped around the front of the thigh, pulled snug and then secured by VELCRO fasteners (not shown).

In a presently preferred embodiment, a pair of hinge pads 98, 100 are mounted by rivets or similar fasteners to the femoral link elements 38 of linkages 24, 26, respectively. These hinge pads 98, 100 protect the knee 20 from contact with the hinge 42 or the femoral or tibial link elements 38, 40.

The lower half of the four-point suspension system which mounts the brace 10 to the leg of the patient is illustrated in FIGS. 1 and 3. A tibial cuff strap 102 is provided to mount the tibial cuff 18 to the calf 14. The ends of the tibial cuff strap 102 have VELCRO strips 104, 106 mounted to their inner and outer surfaces, respectively. One end of the tibial cuff strap 102 supports a VELCRO strip 108 on its inner surface. The tibial cuff strap 102 is mounted to the tibial cuff 18 by connecting the VELCRO strip 108 to a cooperating VELCRO strip 110 on one side of tibial cuff 18, wrapping the strap 102 about the posterior aspect of the calf 14 and then connecting the strip 104 on the inner surface of the opposite end of strap 102 to the strip 106 on the outer surface of the strap 102. Preferably, the strap 102 is formed of the same relatively high friction, elastic material as femoral cuff strap 86.

A tibial pad 112 formed of flexible, cushion material is mounted at the distal-most end of the tibial cuff 18 by a substantially inelastic strap 114. One end of the strap 114 is carried by a ring 116 riveted to the sleeve 34 at one side of the tibial cuff 18, and the opposite end of strap 114 is carried by a ring 118 riveted to the sleeve 36 at the opposite side of tibial cuff 18. The ends of strap 114 have VELCRO strips 120 which are connected to a cooperating VELCRO strip 124 on the outer surface of strap 114 (the side opposite tibial pad 112) to secure the tibial pad 86 to the calf 14.

The four-point suspension system described above for mounting the femoral and tibial cuffs 16, 18 to the leg provides for the imposition of a posterior restraining force on the tibia 23 for assisting patients having anterior cruciate ligament deficiencies. The magnitude of the posterior restraining force applied by the brace 10 to the tibia 23 is adjustable by varying the position of the pivot axis of the brace, i.e., hinge 42 in FIGS. 1-5, 7 and 8 or the cam 168 in FIGS. 6A-C, in an anterior-posterior direction and/or a proximal-distal direction with respect to the flexion-extension axis 22 of the knee 20. The magnitude of this posterior restraining force depends upon the extent of posterior and/or proximal-distal misalignment between the hinge axis 64 and flexion axis 22, which is varied according to the amount of abnormal joint looseness and the compliance of the soft tissues of the leg. Generally, the greater the amount of posterior and distal misalignment between the hinge axis 64 and flexion axis 22, the greater the posterior force applied to the tibia 23 as the knee 20 is extended.

Considering first the anterior-posterior location on the femur of the brace pivot axis, the brace 10 of this invention includes two alternatives for accomplishing an adjustment in such direction. Referring to FIGS. 1 and 1A, the femoral link element 38 is pivotally mounted to the femoral cuff 16 by a pin 48. This permits pivoting or angular movement of the femoral link element 38 about the pin 48 relative to the femoral cuff 16. By pivoting the femoral link element 38 in a posterior direction, the hinge 42 and, in turn, the hinge axis 64 of brace 10, is positioned posteriorly relative to the flexion-extension axis 22 of the knee 20. The femoral link element 38 is then held in fixed position at this location by the straps 86 and 87 described above.

An alternative anterior-posterior adjustment structure is illustrated in FIGS. 6A-C. In this embodiment, the brace pivot axis is defined by the center of cam 168 where the pivot arm 188 pivots about pin 190 in response to movement of the tibial link element 180. The location of the pin 190, and hence the center of rotation of pivot arm 180, can be adjusted in an anterior-posterior direction by rotating the cam 168 about the screw 174 which is offset or eccentrically positioned relative to the center of the cam 168. That is, by loosening screw 174 which connects the cam 168 to the femoral link element 170, the cam can be rotated in a clockwise or counterclockwise direction which, in turn, changes the anterior-posterior position of the pin 190.

For example, as shown in FIG. 6C, the cam 168 has been rotated in a counterclockwise direction about screw 174 so as to position the pin 190 of connector bar 188 at an angle 192 relative to the longitudinal axis of the femoral link element 170, compared to the position of pin 190 in FIGS. 6A and 6B. Once the anterior-posterior position of the pin 190 is determined, depending upon the magnitude of posterior or anterior restraining force desired, the screw 174 is then retightened to maintain the cam 168 in a fixed position relative to the femoral link element 170.

As mentioned above, the magnitude of the posterior restraining force applied by the brace 10 to the knee 20 is also dependent, to some extent, upon the location of the brace pivot axis in a proximal-distal direction on the femur relative to the flexion-extension axis 22 of the knee 20. Such proximal-distal adjustment of the brace pivot axis, i.e., either the pivot axis 64 of hinge 42 or the center 190 of cam 168, can be achieved, for example, with the structure illustrated in FIGS. 7 and 8 herein.

Figure 7:
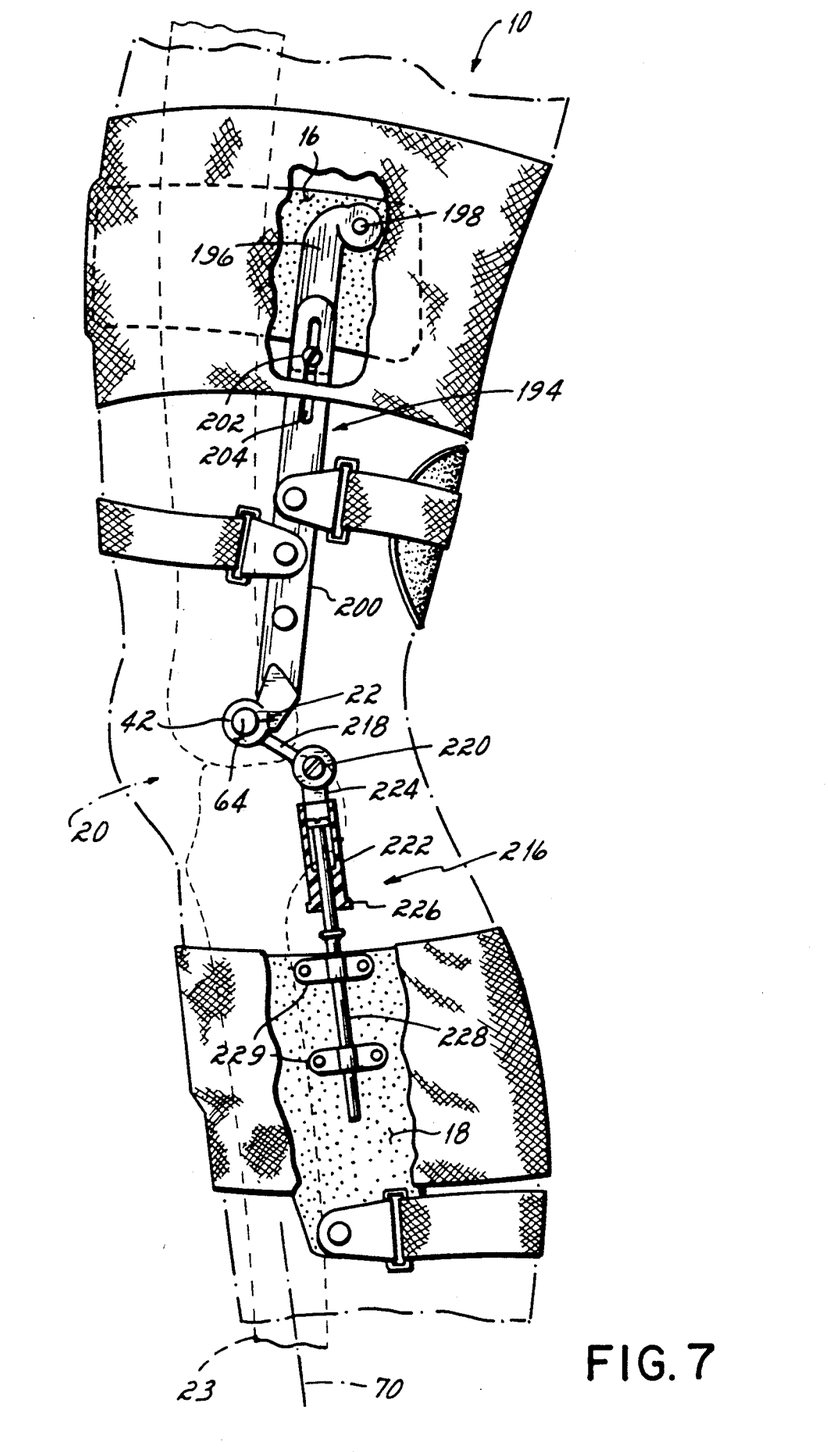
FIG. 7 is a view of the knee brace herein including one embodiment of structure for varying the proximal-distal position on the femur of the brace pivot axis and corresponding adjustment structure for varying the anterior-posterior position on the tibia of the proximal end of the tibial link elements.

Referring first to FIG. 7, a femoral link element 194 is formed with an upper bar 196 connected by a pin 198 to the femoral cuff 16, and a lower bar 200 connected to the hinge 42. The upper and lower bars 196, 200 are interconnected by a screw 202 which extends from the upper bar 196 and through an elongated slot 204 formed in the lower bar 200. The proximal-distal position of the hinge 42 is varied by loosening screw 202, moving the lower bar 200 relative to the upper bar 196 and then retightening the screw 202.

Figure 8:
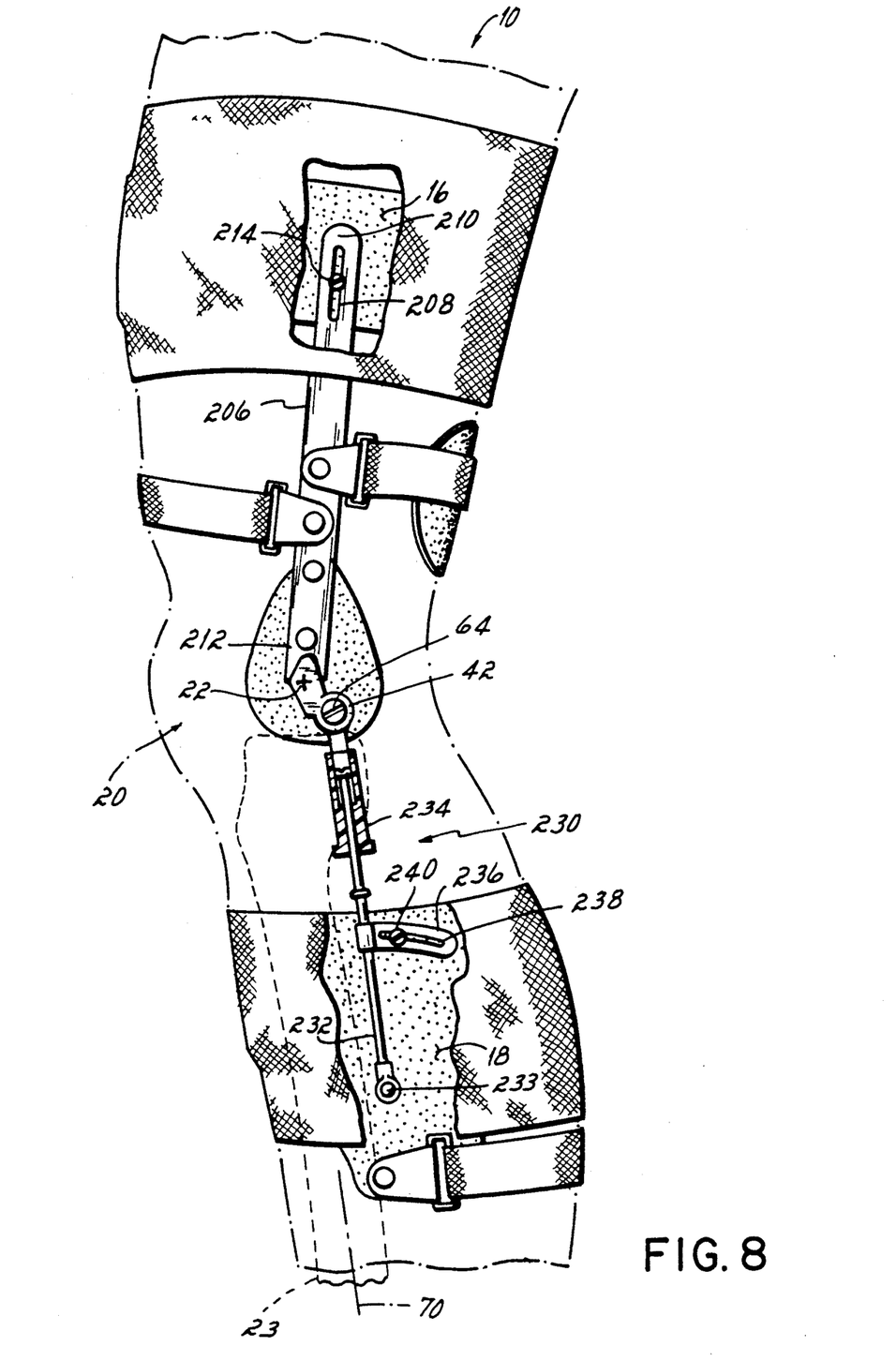
FIG. 8 is a view similar to FIG. 7 of an alternative embodiment of the proximal-distal adjustment structure for the femoral link elements and corresponding alternative adjustment structure to vary the anterior-posterior position on the tibia of the proximal end of the tibial link elements.

A variation of the aforementioned proximal-distal adjustment is illustrated in FIG. 8 wherein a femoral link element 206 is formed with an elongated slot 208 at its proximal end 210. The distal end 212 of the femoral link element 206 is mounted to hinge 42. The proximal end 210 of femoral link element 206 is mounted to the femoral cuff 16 by a screw 214 and adjustment of the proximal-distal position of the hinge 42 relative to the femoral cuff 16 is achieved by moving the femoral link element 206 relative to the screw 214 along its slot 208.

Proximal-distal adjustment of the position of hinge 42, employing either of the structures shown in FIGS. 7 or 8 as described above, can affect the proper fit of the tibial cuff 18 on the calf of a patient. Normally, the brace 10 is applied to the leg with the patient in a seated position with the knee flexed approximately 90°. With the knee in this position, proximal-distal adjustment of the position of the brace axis 64 of hinge 42 by either proximal-distal movement of the femoral link elements 194 or 206 as described above, or by adjustment of the position of the femoral cuff 16 on the thigh, produces movement of the proximal end of the tibial link element which is connected to hinge 42. This movement of the tibial link element, which is in an anterior-posterior direction on the tibia, can cause the tibial cuff 18 to cock or move away from the calf thus producing an uncomfortable and unacceptable fit. As a result, anterior-posterior adjustment means must be provided for the proximal end of the tibial link element to allow the tibial cuff 18 to lie flat on the calf of the patient.

FIGS. 7 and 8 illustrate two alternative embodiments of structure for adjusting the anterior-posterior position of the proximal end of the tibial link element in response to proximal-distal adjustment of the position of hinge 42. It should be understood that these alternative embodiments could be used interchangeably with the femoral link element 194 or femoral link element 206 of FIGS. 7 and 8, respectively.

Referring to FIG. 7, a tibial link element 216 is provided which comprises an upper bar 218 connected at its proximal end to the hinge 42 and at the distal end to a fixed position pivot 220. A sleeve 222 is connected at its proximal end 224 to the fixed position pivot 220 and its distal end 226 slidably receives a rod 228 carried on the tibial cuff 18 by brackets 229. The sliding motion obtained in the tibial link element 216 is identical to that described in connection with the embodiment of FIG. 4A above, but the addition of the fixed position pivot 220 in this embodiment avoids any cocking or displacement of the tibial cuff 18 in the event of proximal-distal adjustment of the position of hinge 42. This is because the pivot 220 permits anterior-posterior motion of the upper bar 218 relative to the sleeve 222 in response to movement of the hinge 42.

In the alternative embodiment of FIG. 8, a tibial link element 230 has a distal end 232 pivotally mounted by a pin 233 to the tibial cuff 18, and a proximal end axially movable within a sleeve 234 mounted to the hinge 42. An extension 236 formed with an arcuate slot 238 is mounted to the tibial link element 230 part way therealong. A screw 240 extends through the slot 238 in extension 236 and into the tibial cuff 18.

In the event it is desired to adjust the position of hinge 42 in the proximal-distal direction, the screw 240 is first loosened to allow the tibial link element 230 to pivot about its distal end 232 so that the sleeve 234 at the proximal end of the tibial link element 230 can move with the hinge 42. Once the proximal-distal adjustment of the hinge 42 and corresponding anterior-posterior adjustment of tibial link element 230 are completed, the screw 240 is tightened to maintain the tibial link element 230 in a fixed, adjusted position.

The posterior restraining force applied by the brace 10 to the tibia 23 with the hinge axis 64 of hinge 42 or center 190 of cam 168 located posteriorly, and possibly distally, relative to the knee flexion axis 22 imposes an initial force which compresses the soft tissue of the leg as the knee 20 is extended by the quadricep muscles. When the patient then continues the activity which loads the tibia 23 and tends to create anterior movement thereof, the brace 10 can develop an additional restraining force with little additional tibial displacement because the soft tissue has already been compressed and has sufficient stiffness to allow the brace to prevent further anterior displacement of the tibia. As the knee is extended, this posterior restraining force increases and is greatest at full extension where the anterior cruciate ligament normally provides its greatest restraint to anterior tibial translation.

Although the hinge axis 64 of hinge 42 and/or the pivot axis 190 of cam 168 are misaligned from the flexion axis 22 of the knee joint 20, as illustrated in FIGS. 1A and 6C, the sliding connection between the tibial link elements 40 or 180 prevent the application of forces by the brace 10 to the knee 20 in a direction substantially parallel to the longitudinal axis of the tibia.

While the invention has been described with reference to a preferred embodiment, it will be understood by those skilled in the art that various changes may be made and equivalents may be substituted for elements thereof without departing from the scope of the invention.

For example, the particular configuration of the hinge 42 may be modified in a number of ways and still achieve the desired result of pivotally interconnecting the linkage assemblies 24, 26. Moreover, adjustment of the position of the hinge 42 posteriorly of the flexion-extension axis 22 of the knee joint 20 can be accomplished in other ways such as by fixedly mounting the femoral link elements 38 to the femoral cuff 16 and providing a hinge structure having an adjustable hinge axis. Additionally, posterior cruciate ligament deficiencies can be accommodated by the brace 10 of this invention by positioning the hinge axis 64 anteriorly relative to the flexion axis 22, as shown in phantom in FIG. 1A, and changing the position of the straps which mount the femoral cuff 16 and tibial cuff 18 to the leg.

Therefore, it is intended that the invention not be limited to the particular embodiment disclosed as the best mode contemplated for carrying out this invention, but that the invention will include all embodiments falling within the scope of the appended claims.

We claim:

1. A knee brace, comprising:

a femoral cuff having opposed sides and being adapted to mount onto the thigh of a patient;

a tibial cuff having opposed sides and being adapted to mount onto the calf of a patient;

a pair of linkage means for interconnecting said femoral cuff and said tibial cuff, each of said linkage means having a first link element mounted to one side of said femoral cuff and a second link element mounted to one side of said tibial cuff;

a pair of hinge means for pivotally connecting said first and second link elements of each of said linkage means, each of said hinge means having a hinge axis which is not aligned with the flexion-extension axis of the knee during at least some portion of the range of motion of the knee with the knee brace mounted to the leg of a patient;

mounting means, cooperating with said femoral cuff and said tibial cuff, for causing a brace force to be applied to the lower leg of the patient having a force component which resists anterior or posterior movement of the lower leg relative to the upper leg of the patient;

slider means associated with said second link element of each said linkage means for permitting axial movement of at least a portion of said second link element relative to the tibia along an axis substantially parallel to the longitudinal axis of the tibia with the knee brace mounted to the leg of the patient, said slider means substantially preventing a force component of said brace force from acting along said longitudinal axis of said tibia.

2. The knee brace of claim 1 in which each of said first link elements has a proximal end pivotally mounted to one side of said femoral cuff.

3. The knee brace of claim 1 in which said slider means associated with each of said second link elements comprises:
a rod having a proximal end connected to said hinge means; and
a hollow sleeve carried on said tibial cuff, said rod being axially movable within said hollow sleeve.

4. The knee brace of claim 3 in which said sleeve of said slider means is formed with a stop to limit the extent of axial movement of said sleeve relative to said rod.

5. The knee brace of claim 3 in which said rod and said sleeve are cylindrical in shape, said sleeve being rotatable with respect to said rod.

6. The knee brace of claim 3 in which said hollow sleeve of each said slider means is formed with a stepped throughbore defining a shoulder in each of said sleeves, said rod of each said slider means having a stop at one end axially movable within said stepped throughbore of each of said hollow sleeves, said stop engaging said shoulder formed in said hollow sleeves to prevent disengagement of said rods from said sleeves.

7. The knee brace of claim 1 in which said slider means associated with each of said second link elements comprises:
a hollow sleeve having a proximal end connected to said hinge means; and
a rod mounted to said tibial cuff, said rod being axially movable within said hollow sleeve.

8. The knee brace of claim 7 in which said rod and said sleeve are cylindrical in shape, said rod being rotatable with respect to said sleeve.

9. The knee brace of claim 1 in which said slider means associated with each of said second link elements comprises:
an upper bar having a distal end, and a proximal end connected to said hinge means;
a lower bar having a distal end mounted to said tibial cuff and a proximal end formed with a slot, said distal end of said upper bar being positionable adjacent said proximal end of said lower bar;
a connector plate having fastener means extending through said slot in said lower bar and into fixed engagement with said upper bar, said lower bar being axially movable relative to said upper bar as said fastener means slides along said slot formed in said lower bar.

10. The knee brace of claim 24 in which said slider means associated with each of said second link elements comprises:
a cam mounted to said first link element, said cam being formed with a circumferential groove in its peripheral edge;
a bar having a distal end pivotally mounted to said tibial cuff, and a proximal end slidable along said circumferential groove in said peripheral edge of said cam;
an arm pivotally mounted at one end to said cam, said arm having an opposite end which engages said bar to retain said bar within said circumferential groove.

11. The knee claim of claim 10 in which said first link element is mounted to said cam at a point offset from the center of said cam.

12. The knee brace of claim 10 in which said arm is U-shaped having an open end and a closed end, said open end of said arm being pivotally connected to the center of said cam and said closed end thereof being located about said bar to retain said bar within said circumferential groove in said cam.

13. A knee brace, comprising:
a femoral cuff having opposed sides and being adapted to mount onto the thigh of a patient;
a tibial cuff having opposed sides and being adapted to mount onto the calf of a patient;
a pair of linkage means for interconnecting said femoral cuff and said tibial cuff, each of said linkage means having a femoral link element and having a tibial link element mounted to one side of said tibial cuff;
a pair of hinge means for pivotally connected said femoral link element and said tibial link element of each said linkage means, each of said hinge means having a hinge axis;
means for mounting said femoral link element of each of said linkage means to one side of said femoral cuff, said means permitting misalignment of the position of said hinge axis of said hinge means with respect to the flexion-extension axis of the knee with the brace mounted to the leg of a patient along an axis generally perpendicular to the longitudinal axis of the tibia when the knee is at 0° flexion;
mounting means, cooperating with said femoral cuff and said tibial cuff, said causing a brace force to be applied to the lower leg of the patient having a force component which resists anterior or posterior movement of the lower leg relative to the upper leg of the patient;
slider means associated with said second link element of each said linkage means for permitting axial movement of at least a portion of said second link element relative to the tibia along an axis substantially parallel to the longitudinal axis of the tibia with the knee brace mounted to the leg of the patient, said slider means substantially preventing a force component of said brace force from acting along said longitudinal axis of said tibia.

14. The knee brace of claim 13 in which said means for permitting variation of the position of said hinge axis of said hinge means comprises:
  a pin pivotally mounting one end of each of said femoral link elements to one side of said femoral cuff, said femoral link elements being pivotal about said pin to vary the position of said hinge connected thereto.

15. The knee brace of claim 13 in which said means for permitting variation of the position of said hinge axis of said hinge means comprises a slot formed in the proximal end of each said femoral link elements, and a screw insertable through said slot and into said femoral cuff.

16. The knee brace of claim 13 in which said means for permitting variation of the position of said hinge axis of said hinge means comprises:
  an upper bar pivotally mounted to said femoral cuff;
  a lower bar mounted to one end to said hinge means and being formed with a slot at the other end;
  a fastener insertable through said slot in said lower bar and into said upper bar, said lower bar being movable relative to said upper bar along said slot therein to vary the position of said hinge axis of said hinge means connected to said lower bar relative to said femoral cuff.

17. A knee brace, comprising:
  a femoral cuff having opposed sides and being adapted to mount onto the thigh of a patient;
  a tibial cuff having opposed sides and being adapted to mount onto the calf of a patient;
  a pair of linkage means for interconnecting said femoral cuff and said tibial cuff, each of said linkage means including a femoral link element having a proximal end anda distal end, and a tibial link element having a proximal end and a distal end;
  a pair of hinge means for pivotally interconnecting said distal end of said femoral link element and said proximal end of said tibial link element of each said linkage means, each of said hinge means having a hinge axis;
  means for mounting said proximal end of said femoral link element of each said linkage means to one side of said femoral cuff;
  means associated with said femoral link element of each said linkage means for varying the position of said hinge axis of said hinge means in a direction toward or away from said femoral cuff;
  means associated with said tibial link element of each said linkage means for varying the position of said proximal end of said tibial link elements along an axis substantially perpendicular to the longitudinal axis of the tibia;
  mounting means, cooperating with said femoral cuff and said tibial cuff, for causing a brace force to be applied to the lower leg of the patient having a force component which resists anterior or posterior movement of the lower leg relative to the upper leg of the patient;
  slider means associated with said second link element of each said linkage means for permitting axial movement of at least a portion of said second link element relative to the tibia along an axis substantially parallel to the longitudinal axis of the tibia with the knee brace mounted to the leg of the patient, said slider means substantially preventing a force component of said brace force from acting along said longitudinal axis of said tibia.

18. The knee brace of claim 17 in which said means for varying the position of said proximal end of said tibial link element of each said linkage means comprises:
  an adjustable position pivot;
  an upper bar connected between said hinge means and said adjustable position pivot;
  lower linkage means having a proximal end connected to said adjustable position pivot and a distal end connected to said tibial cuff, said adjustable position pivot permitting movement of said upper bar and said proximal end of said lower linkage means in a direction generally perpendicular to the longitudinal axis of the tibia with the knee brace mounted to the leg of a patient.

19. The knee brace of claim 17 in which said means for varying the position of said proximal end of said tibial link element of each said linkage means comprises:
  an extension formed with a slot mounted to said distal end of said tibial link element; and
  a fastener extending through said slot in said extension and into said tibial cuff, said tibial link element being movable relative to said tibial cuff along said slot formed in said extension to vary the position of said proximal end of said tibial link element along an axis substantially perpendicular to the longitudinal axis of the tibia with the knee brace mounted to the leg of a patient.

20. The knee brace of claim 17 in which said means for varying the position of said hinge axis of said hinge means relative to said femoral cuff comprises a slot formed in the proximal end of each said femoral link elements, and a screw insertable through said slot and into said femoral cuff.

21. The knee brace of claim 17 in which said means for varying the position of said hinge axis of said hinge means comprises:
  an upper bar pivotally mounted to said femoral cuff;
  a lower bar mounted at one end to said hinge means and being formed with a slot at the other end;
  a fastener insertable through said slot in said lower bar and into said upper bar, said lower bar being movable relative to said upper bar along said slot therein to vary the position of said hinge axis of said hinge means connected to said lower bar relative to said femoral cuff.

22. A knee brace, comprising:
  a femoral cuff adapted to mount onto the thigh of a patient;
  a tibial cuff adapted to mount onto the calf of a patient;
  linkage means for interconnecting said femoral cuff and said tibial cuff, said linkage means having a first link element mounted to said femoral cuff and a second link element mounted to said femoral cuff;
  hinge means for pivotally connected said first and second link elements of said linkage means, said hinge means having a hinge axis which is not aligned with the flexion-extension axis of the knee during at least some portion of the range of motion of the knee with the knee brace mounted to the leg of a patient;

mounting means, cooperating with said femoral cuff and said tibial cuff, for causing a brace force to be applied to the lower leg of a patient having a force component which resists anterior or posterior movement of the lower leg relative to the upper leg of the patient;

slider means associated with said second link element of each said linkage means for permitting axial movement of at least a portion of said second link element relative to the tibia along an axis substantially parallel to the longitudinal axis of the tibia with the knee brace mounted to the leg of the patient, said slider means substantially preventing a force component of said brace force from acting along said longitudinal axis of said tibia.

23. A knee brace, comprising:

a femoral cuff having opposed sides and being adapted to mount onto the thigh of a patient;

a tibial cuff having opposed sides and being adapted to mount onto the calf of a patient;

a pair of linkage means for interconnecting said femoral cuff and said tibial cuff, each of said linkage means having a femoral link element, and a tibial link element mounted to one side of said tibial cuff;

a pair of hinge means for pivotally connecting said femoral and tibial link elements of each of said linkage means, each of said hinge means having a hinge axis;

means for mounting said femoral link element of each of said linkage means to one side of said femoral cuff, said means permitting variation of the position of said hinge axis of said hinge means along an axis generally perpendicular to the longitudinal axis of the tibia with the brace mounted to the leg of the patient and when the knee is at 0° of flexion;

mounting means, cooperating with said femoral cuff and said tibial cuff, for causing a brace force to be applied to the lower leg of the patient having a force component which resists anterior or posterior movement of the lower leg relative to the upper leg of the patient;

slider means associated with said second link element of each said linkage means for permitting axial movement of at least a portion of said second link element relative to the tibia along an axis substantially parallel to the longitudinal axis of the tibia with the knee brace mounted to the leg of the patient, said slider means substantially preventing a force component of said brace force from acting along said longitudinal axis of said tibia.

* * * * *